(12) United States Patent
Takasaki

(10) Patent No.: US 11,638,565 B2
(45) Date of Patent: May 2, 2023

(54) RADIOGRAPHIC IMAGING APPARATUS AND CONTROL METHOD THEREFOR

(71) Applicant: CANON KABUSHIKI KAISHA, Tokyo (JP)

(72) Inventor: Takashi Takasaki, Saitama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 273 days.

(21) Appl. No.: 17/088,445

(22) Filed: Nov. 3, 2020

(65) Prior Publication Data

US 2021/0068774 A1    Mar. 11, 2021

Related U.S. Application Data

(63) Continuation of application No. PCT/JP2019/016806, filed on Apr. 19, 2019.

(30) Foreign Application Priority Data

May 11, 2018   (JP) .............................. JP2018-092233

(51) Int. Cl.
*A61B 6/00*     (2006.01)
*H04N 5/32*     (2006.01)
*G06T 5/00*     (2006.01)

(52) U.S. Cl.
CPC .............. *A61B 6/4208* (2013.01); *A61B 6/52* (2013.01); *A61B 6/54* (2013.01); *G06T 5/001* (2013.01);

(Continued)

(58) Field of Classification Search
CPC ......... A61B 6/469; A61B 6/06; A61B 6/5205; A61B 6/5258; A61B 6/025; A61B 6/586;
(Continued)

(56) References Cited

U.S. PATENT DOCUMENTS

2009/0160979 A1    6/2009   Xu
2014/0036118 A1    2/2014   Dowaki et al.
(Continued)

FOREIGN PATENT DOCUMENTS

EP    0 590 719 A2    4/1994
JP    3196033 B2 *    8/2001
(Continued)

*Primary Examiner* — Don K Wong
(74) *Attorney, Agent, or Firm* — Canon U.S.A., Inc. IP Division

(57) ABSTRACT

A radiographic imaging apparatus includes: an effective pixel area including a plurality of detection areas, in each of which a first pixel including a photoelectric conversion element and a second pixel including a light-blocking element are provided; a plurality of signal processing units that are provided so as to correspond to the plurality of detection areas and each process, for a corresponding one of the detection areas, an output signal from the first pixel and an output signal from the second pixel provided in the corresponding one of the detection areas; and a correction unit that makes, for each signal processing unit among the plurality of signal processing units, a correction to the output signal from the first pixel processed by the signal processing unit, by using the output signal from the second pixel processed by the signal processing unit.

15 Claims, 5 Drawing Sheets

(52) U.S. Cl.
CPC ...... *H04N 5/32* (2013.01); *G06T 2207/10116* (2013.01); *G06T 2207/30004* (2013.01)

(58) Field of Classification Search
CPC ..... A61B 6/4233; A61B 6/463; A61B 6/5211; A61B 6/5217; A61B 6/4291; A61B 6/585; A61B 2090/3762; A61B 6/03; A61B 6/4266; A61B 6/4417; A61B 6/482; G06T 2207/10116; G06T 11/005; G06T 2207/10081; G01T 1/20; G01N 23/046; G01N 2223/304; G01N 2223/505; G01N 23/2255
See application file for complete search history.

(56) References Cited

U.S. PATENT DOCUMENTS

2016/0028976 A1  1/2016  Ran
2018/0108118 A1  4/2018  Takahashi

FOREIGN PATENT DOCUMENTS

| JP | 2007019820 A | 1/2007 |
| JP | 2008 237835 A | 10/2008 |
| JP | 2016-152550 A | 8/2016 |
| JP | 2016-201634 A | 12/2016 |
| JP | 2017163233 A | 9/2017 |

\* cited by examiner

RADIOGRAPHIC IMAGING APPARATUS AND CONTROL METHOD THEREFOR

CROSS-REFERENCE TO RELATED APPLICATIONS

This application is a Continuation of International Patent Application No. PCT/JP2019/016806, filed Apr. 19, 2019, which claims the benefit of Japanese Patent Application No. 2018-092233, filed May 11, 2018, both of which are hereby incorporated by reference herein in their entirety.

TECHNICAL FIELD

The present invention relates to a radiographic imaging apparatus that captures images of an object by using radiation, and a control method therefor.

BACKGROUND ART

As a radiographic imaging apparatus used to perform medical diagnostic imaging or non-destructive inspection by using radiation, such as X rays, a radiographic imaging apparatus in which a matrix substrate including pixels, each of which is a combination of a conversion element, such as a photoelectric conversion element, and a switch element, such as a TFT (thin film transistor), and which are arranged in a matrix, is used is in practical use. In this radiographic imaging apparatus in which the plurality of conversion elements are provided, the value of output (that is, offset output) when irradiation is not performed at all (zero irradiation) varies to some extent among the pixels due to differences in the environment, such as the temperature. It is preferable to correct such variations in output in order to obtain a radiographic image of clean image quality.

As an existing method for correcting the offset output, for example, PTL 1 describes a method in which a light-blocking optical black area for obtaining an offset signal is provided in an effective pixel area in addition to conversion elements for obtaining a radiographic image signal and the output thereof is used. Specifically, PTL 1 discloses a technique in which a shading of an offset signal from the effective pixel area is grasped from the output from the optical black area in the effective pixel area and the shading is subtracted from a signal from an effective pixel to suppress the shading of the offset signal.

CITATION LIST

Patent Literature

PTL 1 Japanese Patent Laid-Open No. 2007-19820

According to PTL 1, for a shading of an offset signal due to, for example, distribution of the temperature, the amount of image artifact can be reduced by correction. However, with the technique described in PTL 1, in a case where, for example, the effective pixel area is divided into a plurality of detection areas, and a plurality of signal processing units, such as amplifier ICs, for amplifying signals from effective pixels in the respective detection areas are provided, the output of the offset signal may differ among the signal processing units due to, for example, distribution of the temperature. In a case where, for example, the plurality of signal processing units respectively including the amplifier ICs are provided, the gain differs among the amplifier ICs, from which a stepwise difference in the offset signal may arise. That is, with the existing technique, in a case where signals from the effective pixel area are processed by the plurality of signal processing units, there is a problem that an image unevenness based on a difference in the output of the offset signal among the signal processing units occurs in a radiographic image.

SUMMARY OF INVENTION

A radiographic imaging apparatus according to the present invention includes: a pixel area including a plurality of detection areas, in each of which a first pixel that detects radiation and a second pixel that blocks the radiation are provided; a plurality of signal processing units that are provided so as to correspond to the plurality of detection areas and each process, for a corresponding one of the detection areas, an output signal from the first pixel and an output signal from the second pixel provided in the corresponding one of the detection areas; and a correction unit that makes, for each signal processing unit, a correction to the output signal from the first pixel processed by the signal processing unit, by using the output signal from the second pixel processed by the signal processing unit.

Further, the present invention includes a control method for the above-described radiographic imaging apparatus.

Further features of the present invention will become apparent from the following description of exemplary embodiments with reference to the attached drawings.

DESCRIPTION OF EMBODIMENTS

Hereinafter, embodiments of the present invention will be described with reference to the drawings. Note that in the following description of the embodiments of the present invention, a description is given below of a case where an X-ray imaging apparatus that captures X-ray images of an object by using X rays, which is one type of radiation, is assumed to be the radiographic imaging apparatus of the present invention. Further, the present invention is applicable not only to this X-ray imaging apparatus but also to a radiographic imaging apparatus that captures radiographic images of an object by using, for example, another type of radiation (for example, α rays, β rays, or γ rays).

First Embodiment

First, a first embodiment of the present invention is described.

Figure 1:
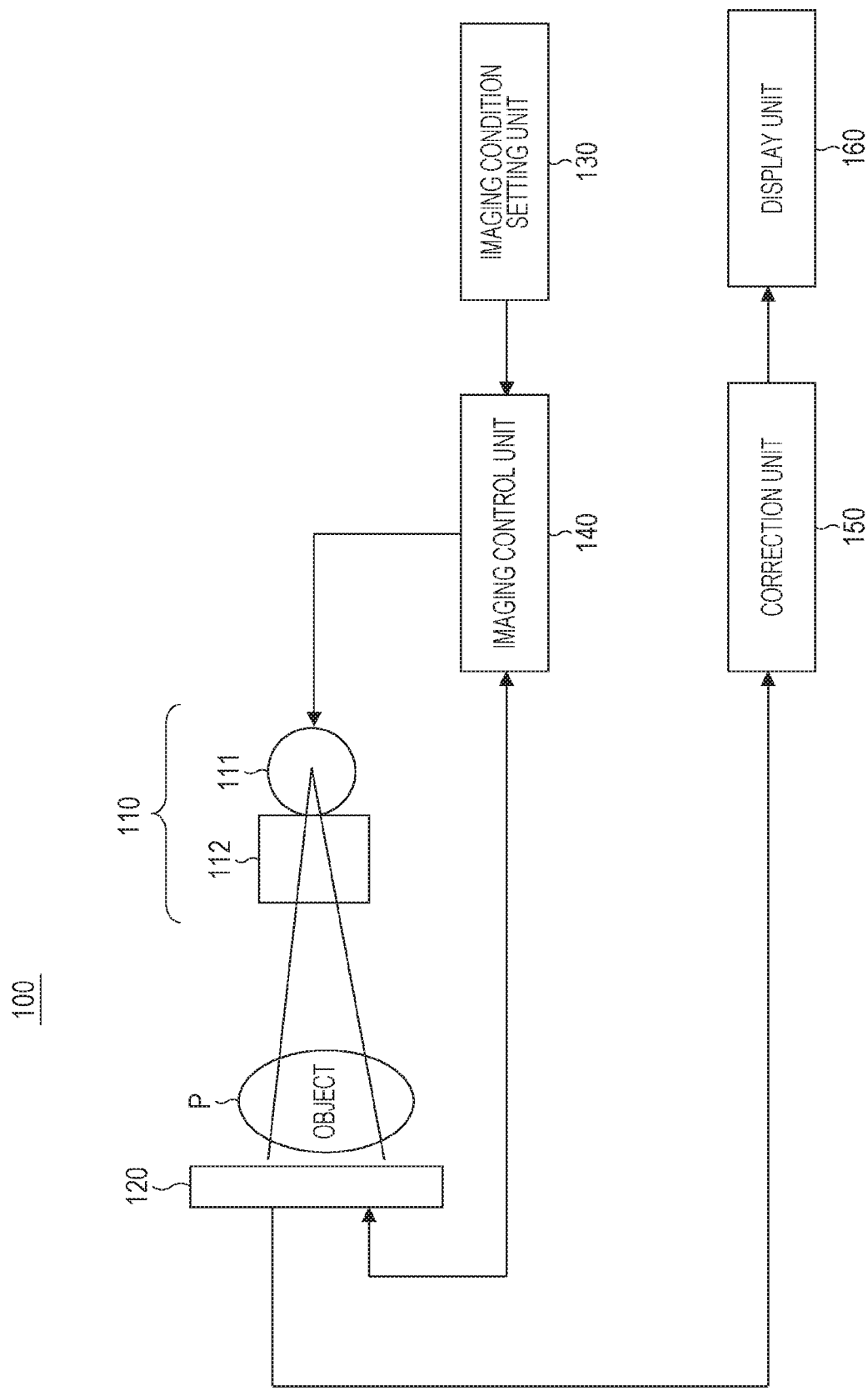
FIG. 1 is a diagram illustrating an example overall configuration of a radiographic imaging apparatus according to a first embodiment of the present invention.

FIG. 1 is a diagram illustrating an example overall configuration of a radiographic imaging apparatus 100 according to the first embodiment of the present invention. It is preferable to use the radiographic imaging apparatus 100 specifically in medical care.

As illustrated in FIG. 1, the radiographic imaging apparatus 100 includes a radiation emission unit 110, a radiation detection unit 120, an imaging condition setting unit 130, an imaging control unit 140, a correction unit 150, and a display unit 160.

The radiation emission unit 110 is a unit that emits radiation (for example, X rays) toward an object P on the basis of control by the imaging control unit 140. This embodiment assumes that the object P is a human body and an imaging region is the hand of the human body. The radiation emission unit 110 includes a radiation generation unit 111 including a radiation tube that generates radiation (for example, X rays) and a collimator 112 that defines the angle of divergence of radiation beams generated in the radiation generation unit 111.

The radiation detection unit 120 is a unit that detects incident radiation (including radiation that passes through the object P) and converts the radiation to a radiographic image signal, which is an electric signal. The radiation detection unit 120 is formed of, for example, an FPD. The internal configuration of the radiation detection unit 120 in this embodiment is described below with reference to FIG. 2.

Figure 2:
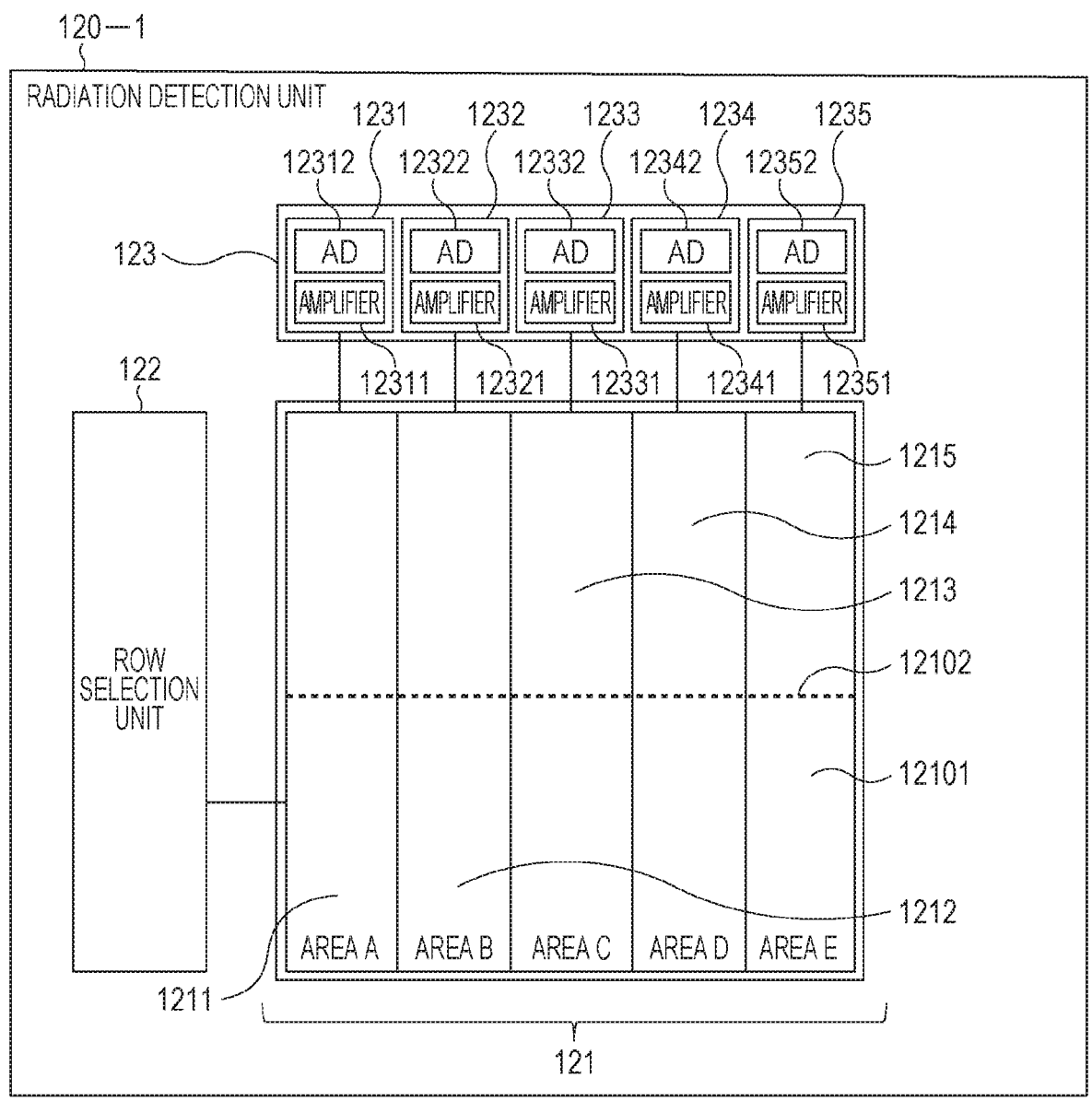
FIG. 2 is a diagram of the first embodiment of the present invention and illustrates an example internal configuration of a radiation detection unit illustrated in FIG. 1.

FIG. 2 is a diagram of the first embodiment of the present invention and illustrates an example internal configuration of the radiation detection unit 120 illustrated in FIG. 1. The radiation detection unit 120 in the first embodiment illustrated in FIG. 2 is referred to as "radiation detection unit 120-1".

As illustrated in FIG. 2, the radiation detection unit 120-1 includes an effective pixel area 121, a row selection unit 122, and a signal converter 123.

As illustrated in FIG. 2, the effective pixel area 121 is an area including a plurality of detection areas A (1211) to E (1215). The effective pixel area 121 is an area in which, for example, pixels are provided in a two-dimensional matrix formed of 500 rows and 500 columns. Specifically, in the effective pixel area 121, in each of the plurality of detection areas A (1211) to E (1215), a plurality of first pixels each including a photoelectric conversion element 12101 and a plurality of second pixels each including a light-blocking element 12102 are provided. FIG. 2 illustrates only the positions of the light-blocking elements 12102 in the effective pixel area 121, and the photoelectric conversion elements 12101 are arranged in a two-dimensional matrix in the other part.

This embodiment assumes that, for example, a scintillator (not illustrated) that converts incident radiation to light is provided between the effective pixel area 121 and the object P, and the photoelectric conversion element 12101 converts the light generated at the scintillator to an electric charge, which is an electric signal. In this embodiment, the plurality of first pixels each including the photoelectric conversion element 12101 function as pixels that detect radiation, and detect a two-dimensional distribution of radiation that reaches the radiation detection unit 120-1 and generate a radiographic image signal (radiographic image data). Each of the first pixels also includes, for example, a switch element that outputs the electric charge (electric signal) accumulated in the photoelectric conversion element 12101 to the signal converter 123 as an output signal.

In this embodiment, the plurality of second pixels each including the light-blocking element 12102 function as pixels that block radiation, and specifically are pixels that block the light generated at the above-described scintillator. Each of the second pixels detects an offset signal included in the radiographic image signal generated by the plurality of first pixels. Further, each of the second pixels also includes, for example, a switch element that outputs the detected offset signal to the signal converter 123 as an output signal. In FIG. 2, the second pixel including the light-blocking element 12102 is discretely arranged in one row of the effective pixel area 121 for every eight columns or nine columns of the first pixels each including the photoelectric conversion element 12101.

Note that in this embodiment, an example is shown where the first pixel including the photoelectric conversion element 12101 that detects light obtained by conversion of incident radiation by the above-described scintillator and the second pixel including the light-blocking element 12102 that blocks the light are formed; however, the present invention is not limited to this form. For example, a form is also applicable to the present invention in which, as the first pixel that detects radiation, a pixel that includes a conversion element converting incident radiation directly to an electric charge, which is an electric signal, instead of the above-described scintillator and the photoelectric conversion element 12101 is formed. Similarly, a form is also applicable to the present invention in which, as the second pixel that blocks radiation, a pixel that includes a blocking element directly blocking incident radiation instead of the above-described scintillator and the light-blocking element 12102 is formed.

The row selection unit 122 selects each row of the effective pixel area 121 on the basis of, for example, control by the imaging control unit 140 and transmits analog signals from the first pixels each including the photoelectric conversion element 12101 and the second pixels each including the light-blocking element 12102 to the signal converter 123 on a per row basis.

The signal converter 123 includes a plurality of signal processing units 1231 to 1235 that are provided so as to correspond to the plurality of detection areas A (1211) to E (1215) and that each process, for a corresponding one of the detection areas, output signals from the first pixels each including the photoelectric conversion element 12101 and the second pixels each including the light-blocking element 12102 provided in the detection area.

Specifically, the signal processing unit 1231 is provided so as to correspond to the detection area A (1211) and processes output signals from the first pixels each including the photoelectric conversion element 12101 and the second pixels each including the light-blocking element 12102 provided in the detection area A (1211). The signal processing unit 1231 includes an amplifier 12311 that amplifies analog signals output from the first pixels and the second pixels in the detection area A (1211) and an AD converter 12312 that converts the analog signals amplified by the amplifier 12311 to digital signals.

The signal processing unit 1232 is provided so as to correspond to the detection area B (1212) and processes output signals from the first pixels each including the photoelectric conversion element 12101 and the second pixels each including the light-blocking element 12102 provided in the detection area B (1212). The signal processing unit 1232 includes an amplifier 12321 that amplifies analog signals output from the first pixels and the second pixels in the detection area B (1212) and an AD converter

12322 that converts the analog signals amplified by the amplifier 12321 to digital signals.

The signal processing unit 1233 is provided so as to correspond to the detection area C (1213) and processes output signals from the first pixels each including the photoelectric conversion element 12101 and the second pixels each including the light-blocking element 12102 provided in the detection area C (1213). The signal processing unit 1233 includes an amplifier 12331 that amplifies analog signals output from the first pixels and the second pixels in the detection area C (1213) and an AD converter 12332 that converts the analog signals amplified by the amplifier 12331 to digital signals.

The signal processing unit 1234 is provided so as to correspond to the detection area D (1214) and processes output signals from the first pixels each including the photoelectric conversion element 12101 and the second pixels each including the light-blocking element 12102 provided in the detection area D (1214). The signal processing unit 1234 includes an amplifier 12341 that amplifies analog signals output from the first pixels and the second pixels in the detection area D (1214) and an AD converter 12342 that converts the analog signals amplified by the amplifier 12341 to digital signals.

The signal processing unit 1235 is provided so as to correspond to the detection area E (1215) and processes output signals from the first pixels each including the photoelectric conversion element 12101 and the second pixels each including the light-blocking element 12102 provided in the detection area E (1215). The signal processing unit 1235 includes an amplifier 12351 that amplifies analog signals output from the first pixels and the second pixels in the detection area E (1215) and an AD converter 12352 that converts the analog signals amplified by the amplifier 12351 to digital signals.

The radiation detection unit 120-1 illustrated in FIG. 2 transmits signals processed by the signal processing units 1231 to 1235 (specifically, the digital signals processed by the AD converters 12312 to 12352) to the correction unit 150.

Referring back to FIG. 1, a description is further given.

The imaging condition setting unit 130 includes an imaging condition input means for an operator to input imaging conditions including a voltage to be applied to the radiation generation unit (radiation tube) 111 of the radiation emission unit 110, the amount of current, and the radiation emission duration, and transmits imaging condition information input by the operator to the imaging control unit 140.

The imaging control unit 140 controls the radiation emission unit 110 and the radiation detection unit 120 on the basis of the imaging condition information transmitted from the imaging condition setting unit 130.

The correction unit 150 corrects, for each signal processing unit among the plurality of signal processing units 1231 to 1235, an output signal that is from the first pixel including the photoelectric conversion element 12101 and that has been processed by the signal processing unit, by using an output signal that is from the second pixel including the light-blocking element 12102 and that has been processed by the signal processing unit. Specifically, the correction unit 150 corrects, for each signal processing unit, an offset signal included in a digital signal obtained by processing the output signal from the first pixel, by using a digital signal obtained by processing the output signal from the second pixel. Thereafter, the correction unit 150 transmits the output signals (digital signals) of the first pixels that have been corrected for each signal processing unit to the display unit 160.

The display unit 160 displays a radiographic image based on the output signals (digital signals) of the first pixels corrected and transmitted from the correction unit 150 on, for example, a monitor. In addition, the display unit 160 can display various types of information, such as imaging condition information transmitted from the imaging condition setting unit 130, as necessary.

Now, a control method for the radiographic imaging apparatus 100 according to this embodiment is described.

Figure 3:
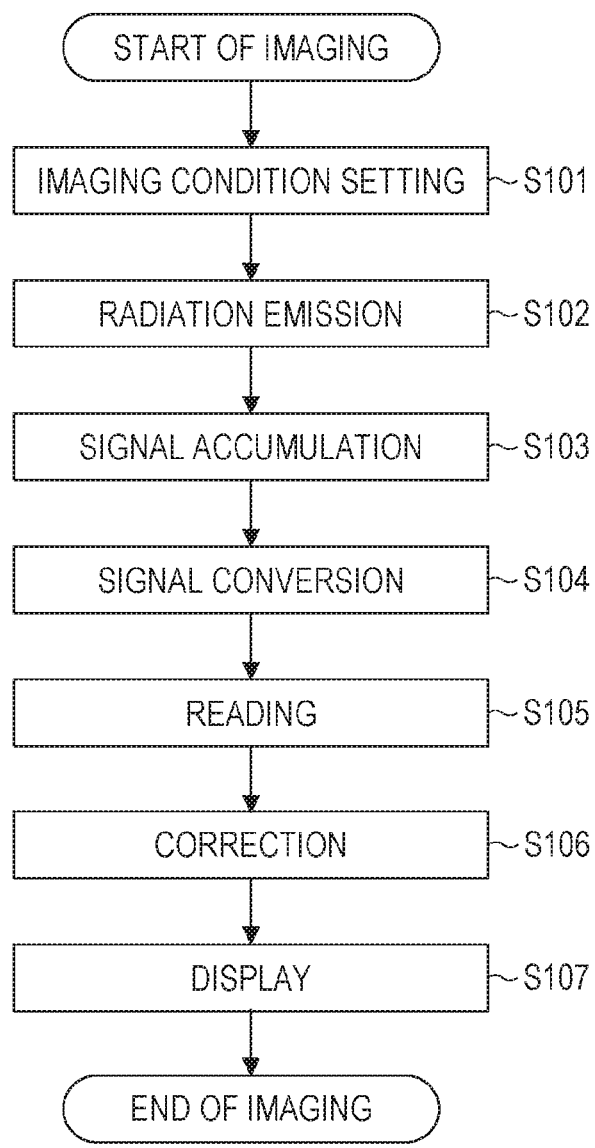
FIG. 3 is a flowchart illustrating an example processing procedure in a control method for the radiographic imaging apparatus according to the first embodiment of the present invention.

FIG. 3 is a flowchart illustrating an example processing procedure in the control method for the radiographic imaging apparatus 100 according to the first embodiment of the present invention.

First, when an instruction for starting imaging of the object P is given, in step S101, the imaging condition setting unit 130 sets imaging conditions input by the operator, the imaging conditions including the tube voltage, tube current, and emission duration in the radiation generation unit (radiation tube) 111. The imaging condition setting unit 130 transmits set imaging condition information to the imaging control unit 140.

Subsequently, in step S102, the imaging control unit 140 controls the radiation emission unit 110 on the basis of the imaging condition information received from the imaging condition setting unit 130 to emit radiation to the object P.

Subsequently, in step S103, the radiation detection unit 120 accumulates electric signals in the first pixels each including the photoelectric conversion element 12101 and the second pixels each including the light-blocking element 12102 in accordance with control by the imaging control unit 140.

Thereafter, after the elapse of the emission duration set in step S101, the imaging control unit 140 controls the radiation emission unit 110 to stop emission of radiation. Next, the imaging control unit 140 transmits an accumulation stop signal for signals to the radiation detection unit 120.

Subsequently, in step S104, when the radiation detection unit 120 receives from the imaging control unit 140 the accumulation stop signal for signals, the row selection unit 122 selects the rows of the effective pixel area 121 one by one and transmits analog signals from the first pixels each including the photoelectric conversion element 12101 and the second pixels each including the light-blocking element 12102 to the signal converter 123 on a per row basis. The row selection unit 122 repeats this operation until transmission of analog signals from all rows in the effective pixel area 121 is completed. At this time, the analog signals from the first pixels and the second pixels in each of the detection areas A (1211) to E (1215) are transmitted to a corresponding one of the signal processing units 1231 to 1235.

Subsequently, in step S105, in the signal converter 123, the amplifiers 12311 to 12351 of the signal processing units 1231 to 1235 perform a process for amplifying the received analog signals of the first pixels and the second pixels. Next, in the signal converter 123, the AD converters 12312 to 12352 of the signal processing units 1231 to 1235 perform a process for converting the analog signals amplified by the amplifiers 12311 to 12351 of the signal processing units 1231 to 1235 to digital signals. Next, the radiation detection unit 120 reads and transmits to the correction unit 150 the digital signals of the first pixels and the second pixels processed by the signal converter 123.

Subsequently, in step S106, the correction unit 150 corrects an offset signal included in the digital signal of the first pixel on the basis of the digital signal of the first pixel including the photoelectric conversion element 12101 and the digital signal of the second pixel including the light-blocking element 12102 received from the radiation detection unit 120. This correction process in step S106 is described with reference to FIG. 4.

FIG. 4 includes diagrams for describing the details of the correction process in step S106 illustrated in FIG. 3. In FIG. 4, configurations similar to those illustrated in FIG. 2 are assigned the same reference numerals, and a detailed description thereof is omitted.

Figure 4A:
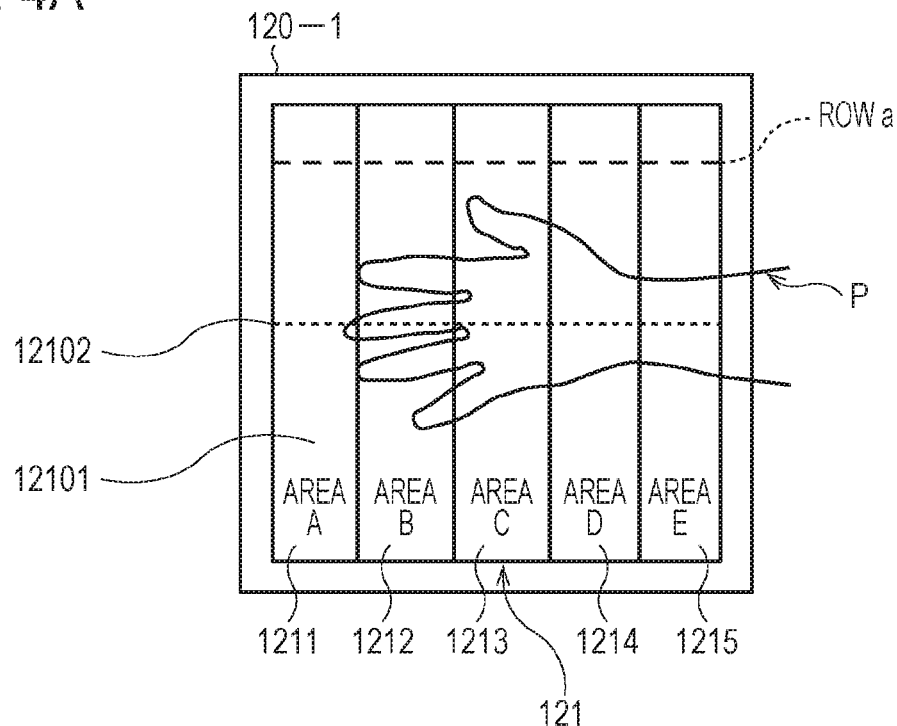
FIG. 4A is a diagram for describing the details of a correction process in step S106 illustrated in FIG. 3.
Figure 4B:
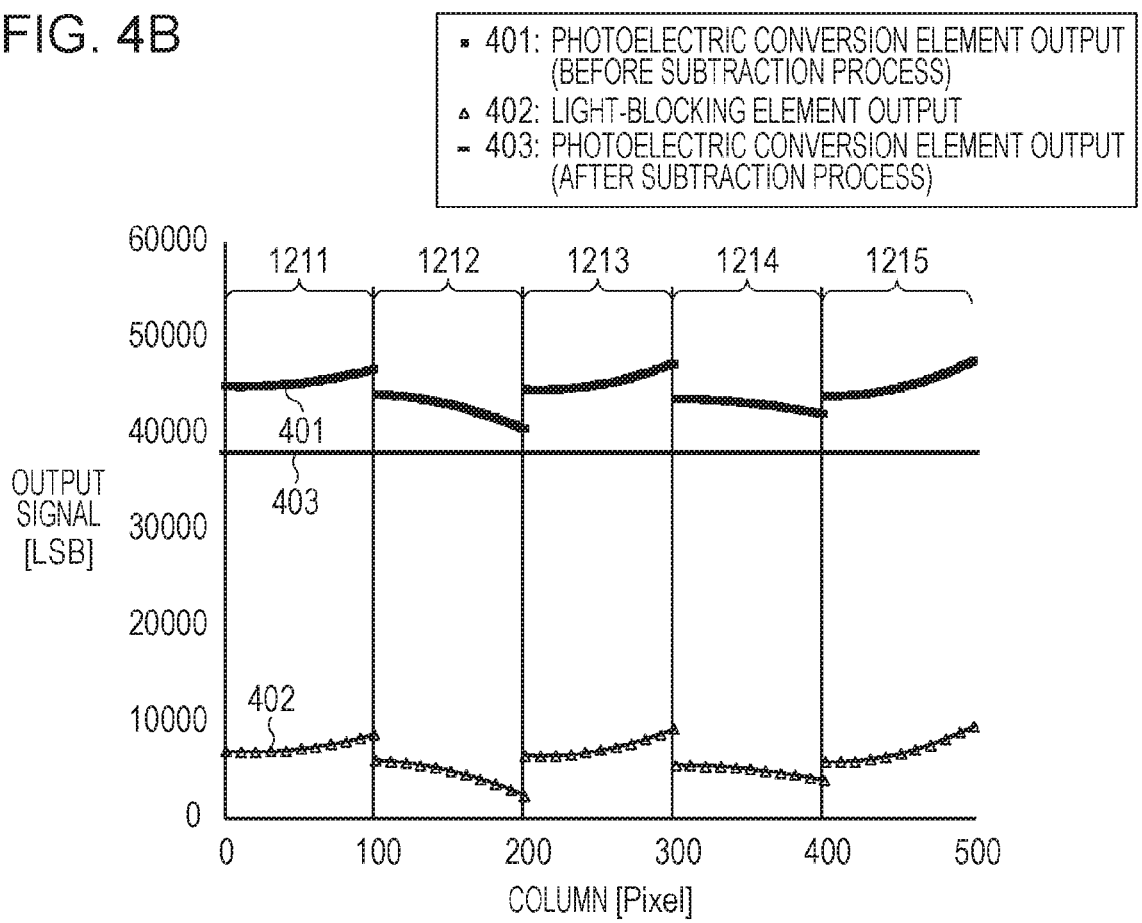
FIG. 4B is a diagram for describing the details of the correction process in step S106 illustrated in FIG. 3.

FIG. 4A is a diagram illustrating the radiation detection unit 120-1 illustrated in FIG. 2 in a simplified manner, and the row selection unit 122 and the signal converter 123 illustrated in FIG. 2 are omitted. FIG. 4B illustrates digital signals in row a illustrated in FIG. 4A among the digital signals of the first pixels each including the photoelectric conversion element 12101, the digital signals having been transmitted in step S105, as photoelectric conversion element output (before subtraction process) 401.

In step S106 in FIG. 3, first, the correction unit 150 performs, for each detection area, an approximation for the digital signals of the second pixels each including the light-blocking element 12102 (arranged for every eight or nine columns) received in step S105 by a quadratic function using the least squares method to interpolate digital signals, thereby making signals for the respective columns. These signals are illustrated in FIG. 4B as light-blocking element output 402.

Next, in step S106 in FIG. 3, for each signal processing unit among the plurality of signal processing units 1231 to 1235, the correction unit 150 makes a correction of subtracting from the digital signal of the first pixel in each row processed by the signal processing unit, the digital signal of the second pixel obtained after the interpolation. In FIG. 4B, the digital signals obtained after performing the process for subtracting the light-blocking element output 402 from the photoelectric conversion element output (before subtraction process) 401 are illustrated as photoelectric conversion element output (after subtraction process) 403.

It is found that in the photoelectric conversion element output (after subtraction process) 403 illustrated in FIG. 4B, a stepwise difference in the signal at each boundary between the detection areas (the vertical line part in FIG. 4B), the stepwise difference being present in the photoelectric conversion element output (before subtraction process) 401 before the subtraction process, and the shading in each detection area are reduced by the subtraction process. Note that in step S106 in FIG. 3, the correction unit 150 performs the subtraction process for the digital signals of the first pixels each including the photoelectric conversion element 12101 for all of the 500 rows. Thereafter, the correction unit 150 transmits the signals obtained after correction to the display unit 160.

When the process in step S106 in FIG. 3 described above ends, the flow proceeds to step S107.

In step S107, the display unit 160 displays a radiographic image based on the output signals (digital signals) of the first pixels corrected and transmitted from the correction unit 150. When the process in step S107 ends, the process in the flowchart illustrated in FIG. 3 ends.

Note that in this embodiment, the following forms are applicable.

As one form, for example, the second pixel including the light-blocking element 12102 may be arranged for every pixel in one row of the effective pixel area 121. In step S106, the moving average of the digital signals of the second pixel may be calculated for a number of neighboring pixels to reduce random noise, thereby making a signal for one column.

As another form, for example, the process from radiation emission in step S102 to reading in step S105 may be repeated a plurality of times, the average of the digital signals of the second pixel for a plurality of frames may be calculated in step S106, and thereafter, interpolation by a quadratic function and the subtraction process may be performed. That is, in this form, the correction unit 150 calculates the average of a plurality of output signals from the second pixel read at different times and makes a correction.

As another form, for example, a form can be employed in which in the correction process in step S106, the correction unit 150 performs a polynomial approximation for output signals from the plurality of second pixels as an interpolation process and corrects output signals from the plurality of first pixels. At this time, for example, the correction unit 150 may perform the above-described interpolation process for each signal processing unit among the signal processing units 1231 to 1235 while changing the order of the above-described polynomial approximation for each of the plurality of division areas obtained by further dividing a corresponding one of the detection areas A (1211) to E (1215) corresponding to the signal processing unit. In this case, it is preferable to use as the order of the polynomial approximation, an order that is determined in accordance with the thermal properties of the radiographic imaging apparatus 100 (for example, the heat generation properties of the radiation detection unit 120). Further, in step S106, at the time of approximation by a quadratic function, a constraint condition may be set such that the output signal from the second pixel including the light-blocking element 12102 in the neighborhood of the detection areas adjacent to each other remains unchanged before and after interpolation. That is, the output signal from the second pixel in the neighborhood of the boundary between the detection areas adjacent to each other remains unchanged before and after the above-described polynomial approximation.

As described above, in the first embodiment, the correction unit 150 corrects, for each signal processing unit among the signal processing units 1231 to 1235 provided so as to correspond to the plurality of detection areas A (1211) to E (1215) in the effective pixel area 121, the output signal that is from the first pixel including the photoelectric conversion element 12101 and that has been processed by the signal processing unit, by using the output signal that is from the second pixel including the light-blocking element 12102 and that has been processed by the signal processing unit.

With the above-described configuration, it is possible to obtain a radiographic image of high image quality giving less uneasy feeling by suppressing an image unevenness caused by processing by the signal processing units. For example, even in a case where a stepwise difference in the offset signal is present at each boundary between the detection areas illustrated in FIG. 4B (the vertical line part in FIG. 4B), with the above-described correction by the correction unit 150, it is possible to obtain a radiographic image of high image quality giving less uneasy feeling. Further, for example, even in a case where a shading occurs in an offset signal for each signal conversion unit due to, for example, distribution of the temperature within the signal conversion unit in addition to the above-described stepwise difference, with the above-described correction by the correction unit 150, it is possible to obtain a radiographic image of high image quality giving less uneasy feeling.

Second Embodiment

Now, a second embodiment of the present invention is described. Note that in the following description of the second embodiment, a description of a matter common to the first embodiment described above is omitted, and a description of a matter different from the first embodiment described above is given.

The overall configuration of the radiographic imaging apparatus according to the second embodiment is similar to the overall configuration of the radiographic imaging apparatus 100 according to the first embodiment illustrated in FIG. 1.

The first embodiment described above is a form in which, as illustrated in FIG. 4, the correction unit 150 uses the output signal from the second pixel including the light-blocking element 12102 and provided in the row direction in the effective pixel area 121 in which pixels are provided in a two-dimensional matrix to correct the output signal from the first pixel including the photoelectric conversion element 12101 in the row direction. The second embodiment is a form in which the correction unit 150 corrects (performs the subtraction process using an offset signal) the output signal from the first pixel including the photoelectric conversion element 12101 in both the row direction and the column direction by using the output signal from the second pixel including the light-blocking element 12102. With the second embodiment, it is possible to further improve the precision of correction of, for example, a shading in an offset signal occurring in two directions, namely, the row direction and the column direction, and to obtain a radiographic image of higher image quality giving less uneasy feeling than in the first embodiment described above.

Figure 5:
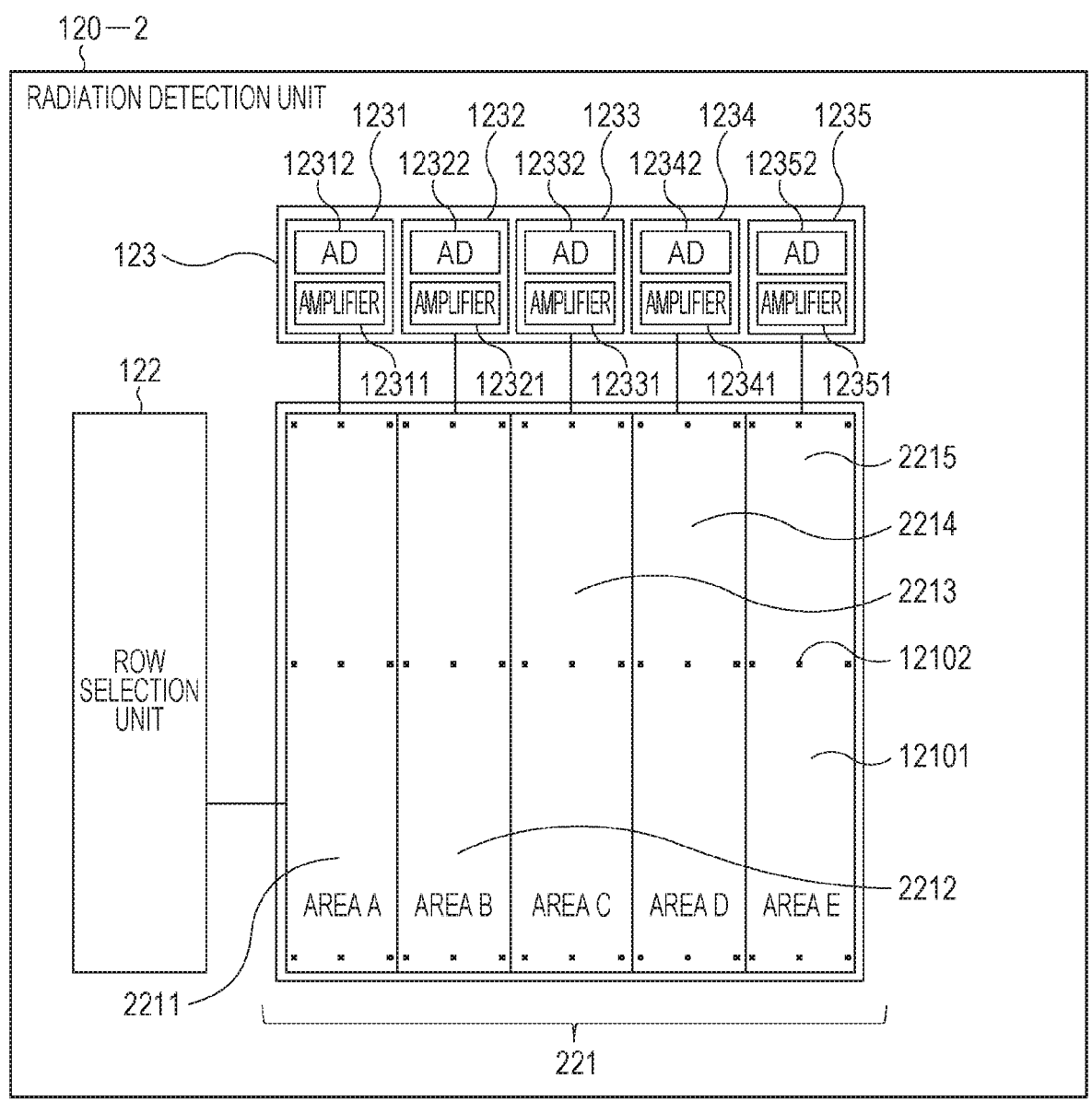
FIG. 5 is a diagram of a second embodiment of the present invention and illustrates an example internal configuration of the radiation detection unit illustrated in FIG. 1.

FIG. 5 is a diagram of the second embodiment of the present invention and illustrates an example internal configuration of the radiation detection unit 120 illustrated in FIG. 1. The radiation detection unit 120 in the second embodiment illustrated in FIG. 5 is referred to as "radiation detection unit 120-2". Further, configurations in FIG. 5 similar to those illustrated in FIG. 2 are assigned the same reference numerals, and a detailed description thereof is omitted.

As illustrated in FIG. 5, the radiation detection unit 120-2 includes an effective pixel area 221, the row selection unit 122, and the signal converter 123. Here, the configuration of the row selection unit 122 and that of the signal converter 123 are similar to the configuration of the row selection unit 122 and that of the signal converter 123 described above with reference to FIG. 2, and therefore, a detailed description thereof is omitted.

As illustrated in FIG. 5, the effective pixel area 221 is an area including a plurality of detection areas A (2211) to E (2215). Specifically, in the effective pixel area 221, in each of the plurality of detection areas A (2211) to E (2215), a plurality of first pixels each including the photoelectric conversion element 12101 and a plurality of second pixels each including the light-blocking element 12102 are provided. FIG. 5 illustrates only the positions of the light-blocking elements 12102 in the effective pixel area 221, and the photoelectric conversion elements 12101 are arranged in a two-dimensional matrix in the other part.

More specifically, in the effective pixel area 221 illustrated in FIG. 5, in each detection area among the detection area A (2211), the detection area B (2212), the detection area C (2213), the detection area D (2214), and the detection area E (2215), the second pixel including the light-blocking element 12102 is arranged at the center of the detection area, in the four corners of the detection area, and at the center position of each of the four sides that form the boundary of the detection area.

In this embodiment, in step S106 in FIG. 3, the correction unit 150 corrects, for each signal processing unit, the output signal from the first pixel processed by the signal processing unit by using the output signal from the second pixel processed by the signal processing unit, in the row direction and the column direction. At this time, the correction unit 150 performs, for example, a process for approximating using the least squares method and interpolating the digital signals of the second pixels each including the light-blocking element 12102 for each detection area in a two-dimensional planar manner. In this case, the correction unit 150 makes a correction of subtracting from the digital signal of the first pixel including the photoelectric conversion element 12101, the digital signal of the second pixel obtained after interpolation and corresponding to the position of the first pixel. In the second embodiment, in the case of two-dimensional planar interpolation, a constraint condition may be set such that the output signals from the six second pixels each including the light-blocking element 12102 in the neighborhood of the detection areas adjacent to each other remain unchanged before and after interpolation. That is, the output signals from the second pixels in the neighborhood of the boundary between the detection areas adjacent to each other remain unchanged before and after the above-described two-dimensional planar approximation.

As described above, with the second embodiment, it is possible to obtain a radiographic image of higher image quality giving less uneasy feeling. For example, with the second embodiment, even in a case where a shading occurs in an offset signal in two directions, it is possible to effectively correct the offset signal for the output signal from the first pixel including the photoelectric conversion element 12101.

Note that as a modification of the second embodiment, the second pixels each including the light-blocking element 12102 provided in the upper part and the lower part of each of the detection areas A (2211) to E (2215) illustrated in FIG. 5 may be arranged outside the effective pixel area 221 as third pixels. This modification can employ a form in which the correction unit 150 makes, for each signal processing unit, the above-described correction using the output signals from the second pixels in the effective pixel area 221 processed by the signal processing unit and the output signals from the third pixels outside the effective pixel area 221 processed by the signal processing unit.

OTHER EMBODIMENTS

The present invention can be implemented as a process in which a program that implements one or more functions in the above-described embodiments is supplied to a system or an apparatus via a network or a storage medium, and one or more processors of a computer of the system or the apparatus read and execute the program. Alternatively, the present invention can be implemented as a circuit (for example, an ASIC) that implements one or more functions.

The program and a computer-readable storage medium storing the program are also included in the present invention.

According to the present invention, it is possible to obtain a radiographic image of high image quality by suppressing an image unevenness caused by processing by signal processing units.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiographic imaging apparatus comprising:
   a pixel area including a plurality of detection areas, in each of which a first pixel that detects radiation and a second pixel that blocks the radiation are provided;
   a plurality of signal processing units that are provided so as to correspond to the plurality of detection areas and each process, for a corresponding one of the detection areas, an output signal from the first pixel and an output signal from the second pixel provided in the corresponding one of the detection areas; and
   a correction unit that makes, for each signal processing unit, a correction to the output signal from the first pixel processed by the signal processing unit, by using the output signal from the second pixel processed by the signal processing unit.

2. The radiographic imaging apparatus according to claim 1, wherein each signal processing unit includes an amplifier that performs a process for amplifying the output signal from the first pixel and the output signal from the second pixel.

3. The radiographic imaging apparatus according to claim 1, wherein each signal processing unit includes an AD converter that performs a process for converting the output signal from the first pixel and the output signal from the second pixel, the output signals being analog signals, to digital signals.

4. The radiographic imaging apparatus according to claim 1, wherein each detection area includes a plurality of first pixels and a plurality of second pixels.

5. The radiographic imaging apparatus according to claim 4, wherein the correction unit makes the correction to output signals from the plurality of first pixels while performing a polynomial approximation for output signals from the plurality of second pixels.

6. The radiographic imaging apparatus according to claim 5, wherein the correction unit makes the correction for each signal processing unit while changing an order of the polynomial approximation for each of a plurality of division areas obtained by dividing a corresponding one of the detection areas corresponding to the signal processing unit.

7. The radiographic imaging apparatus according to claim 6, wherein the order is determined in accordance with a thermal property of the radiographic imaging apparatus.

8. The radiographic imaging apparatus according to claim 5, wherein the output signal from the second pixel in a neighborhood of a boundary between the detection areas adjacent to each other remains unchanged before and after the polynomial approximation.

9. The radiographic imaging apparatus according to claim 4, wherein the correction unit makes the correction to output signals from the plurality of first pixels while calculating moving averages of output signals from the plurality of second pixels.

10. The radiographic imaging apparatus according to claim 4, wherein
    the plurality of first pixels are provided in a two-dimensional matrix in each detection area, and
    the correction unit makes the correction to output signals from the plurality of first pixels processed by a corresponding one of the signal processing units in a row direction and a column direction by using output signals from the plurality of second pixels processed by the corresponding one of the signal processing units.

11. The radiographic imaging apparatus according to claim 10, wherein the correction unit makes the correction to the output signals from the plurality of first pixels while performing a two-dimensional planar approximation for the output signals from the plurality of second pixels.

12. The radiographic imaging apparatus according to claim 11, wherein the output signal from the second pixel in a neighborhood of a boundary between the detection areas adjacent to each other remains unchanged before and after the two-dimensional planar approximation.

13. The radiographic imaging apparatus according to claim 1, wherein the correction unit makes the correction while calculating an average of a plurality of output signals from the second pixel read at different times.

14. The radiographic imaging apparatus according to claim 1, wherein
    a third pixel that blocks the radiation is further provided outside the pixel area, and
    the correction unit makes the correction, for each signal processing unit, by using the output signal from the second pixel processed by the signal processing unit and an output signal from the third pixel processed by the signal processing unit.

15. A control method for a radiographic imaging apparatus, comprising:
    a detection step of detecting radiation by using a pixel area including a plurality of detection areas, in each of which a first pixel that detects the radiation and a second pixel that blocks the radiation are provided;
    a signal processing step of using a plurality of signal processing units that are provided so as to correspond to the plurality of detection areas, and processing, by each signal processing unit, an output signal from the first pixel and an output signal from the second pixel provided in a corresponding one of the detection areas; and
    a correction step of making, for each signal processing unit, a correction to the output signal from the first pixel processed by the signal processing unit, by using the output signal from the second pixel processed by the signal processing unit.

* * * * *